(12) United States Patent
Perlman

(10) Patent No.: US 8,460,738 B1
(45) Date of Patent: Jun. 11, 2013

(54) LIQUID CRYSTALLINE PHYTOSTEROL-GLYCERINE COMPLEX FOR ENHANCED BIOAVAILABILITY AND WATER DISPERSAL

(75) Inventor: Daniel Perlman, Arlington, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 13/464,231

(22) Filed: May 4, 2012

(51) Int. Cl.
*A23D 9/007* (2006.01)

(52) U.S. Cl.
USPC .......................................... 426/611; 426/607

(58) Field of Classification Search
USPC .................................. 426/607, 611
See application file for complete search history.

(56) References Cited

U.S. PATENT DOCUMENTS

| | | | |
|---|---|---|---|
| 6,375,982 B1 * | 4/2002 | Cherukuri | 424/484 |
| 6,406,717 B2 * | 6/2002 | Cherukuri | 424/484 |
| 6,589,556 B2 * | 7/2003 | Cherukuri | 424/484 |
| 7,229,641 B2 * | 6/2007 | Cherukuri | 424/465 |
| 2005/0186155 A1 * | 8/2005 | Raschke et al. | 424/59 |
| 2010/0010101 A1 * | 1/2010 | Cherukuri | 514/770 |

OTHER PUBLICATIONS

Zang, F. et al. 2010 in CAPLUS abstract 153:09319.*

* cited by examiner

*Primary Examiner* — Carolyn Paden
(74) *Attorney, Agent, or Firm* — McLane, Graf, Raulerson & Middleton, PA

(57) ABSTRACT

Edible phytosterol-containing compositions include molecular complexes of non-esterified phytosterols (P) and glycerine (G) in the form of liquid crystalline microparticles. Addition of an emulsifier (M) such as a monoglyceride or a modified lecithin, and optionally an ionic surfactant, to the complex facilitates its dispersal in an aqueous medium. A composition containing either the binary PG or ternary PGM molecular complexes can be formulated as a beverage, food product, or nutritional supplement. When administered to a human subject, the complexes sequester cholesterol in the gastrointestinal tract and reduce LDL cholesterol and total plasma cholesterol levels.

37 Claims, 1 Drawing Sheet

LIQUID CRYSTALLINE PHYTOSTEROL-GLYCERINE COMPLEX FOR ENHANCED BIOAVAILABILITY AND WATER DISPERSAL

BACKGROUND

Cholesterol and phytosterols are very similar in molecular structure and are found in animal and plant cellular membranes, respectively. Both chemical species serve as membrane structural elements and also serve functional roles in living cells. These roles include affecting signal transduction, protein and enzyme binding, membrane elasticity, and a variety of other functions, Cholesterol crystallization has been implicated in pathological conditions ranging from gallstone formation to arterial plaque and lesion formation, Maintaining cholesterol in a soluble or semi-soluble state, rather than a crystalline state, within the cell membrane is important. It remains unclear exactly how this is accomplished within the complexity of a living cell's membrane; however, cholesterol combines with phosphatidylcholine, a phospholipid, which seems to maintain cholesterol solubility. Nevertheless, there are limits to the amount of cholesterol that can be combined with such a phospholipid, beyond which the cholesterol precipitates in crystalline form.

While preventing cholesterol crystallization has health implications and has been the subject of a large number of research studies, the prevention of phytosterol crystallization has been less well studied, since the latter does not relate to a pathological state in humans. However, converting phytosterols from their inherently crystalline state to a soluble or dispersed state, and in a micron-sized or submicron-sized microparticulate form, increases their biological efficacy, which is chiefly to facilitate fecal elimination of cholesterol by admixing with cholesterol in the GI tract. To this end, phytosterols have been combined with a variety of edible solvents, cosolvents, emulsifiers and the like.

Phytosterols including beta-sitosterol, campesterol, stigmasterol and brassicasterol are natural, edible, hydrophobic substances that are commercially isolated from vegetable oils and tall oils. When ingested, these substances mix with dietary and endogenously synthesized cholesterol, and can reduce the amount of cholesterol absorbed into the bloodstream to varying degrees. Like cholesterol, the phytosterols readily crystallize in a variety of morphologies (e.g., needles, plates and rods), all of which are poorly dispersible in water. Compositions and methods have been described which are intended to increase the efficacy of phytosterols in eliminating cholesterol from the gastrointestinal tract. For example, emulsifiers have been used to facilitate the dispersal of non-solubilized phytosterols. One such system is described by Traska et al. in U.S. Pat. No. 6,423,363, which discloses processed foods having an aqueous phase dispersion containing a high melting lipid, such as a phytosterol, that is emulsified with a non-sterol emulsifier. However, dispersions produced from phytosterols and non-sterol emulsifiers that are melting together as described by Traska et al. and dispersed by shear in water typically contain relatively large microparticles (e.g., 10-15 microns). This substantial size that can limit the bioavailability of phytosterols in binding and eliminating cholesterol in the GI tract, as well as the ability to maintain stable suspensions in beverages and other useful compositions. The large size appears to be attributable to the crystalline structure maintained in phytosterol-emulsifier mixed solids formed during cooling of molten mixtures described by Traska et al.

There remains a need to develop compositions that more fully and stably disperse phytosterols in aqueous media for use in food and beverage compositions.

SUMMARY OF THE INVENTION

The invention provides a binary intermolecular complex produced by combining phytosterols that are highly hydrophobic, with glycerine, a highly hydrophilic liquid. The complex is in the form of microparticles with liquid crystalline structure. The complex is formed by heating and melting free phytosterols together with glycerine, during which the phytosterol monohydrate becomes partially or substantially anhydrous. In certain embodiments of the invention, an emulsifier such as a monoglyceride or a modified lecithin is added before cooling the binary complex, thereby forming a ternary or higher order complex that has liquid crystalline structure and is highly dispersible in aqueous media. Forming these liquid crystalline complexes by melting the admixed ingredients together renders the phytosterols water-dispersible for use in beverages, foods and dietary supplements.

The invention further provides ternary complexes containing glycerine, phytosterols, and one or more dispersing agents or emulsifiers, such as monoglycerides (fatty acid monoesters of glycerine). The ternary complexes form microparticles with liquid crystalline structure that can be efficiently dispersed in an aqueous environment. The microparticles can be added to water-containing liquids (e.g., beverages and aqueous foods), can be dispersed as remarkably small microparticles therein.

Thus, one aspect of the invention is an edible composition containing: (i) a non-esterified phytosterol, phytostanol, or a combination thereof (collectively "P"); and (ii) glycerine ("G"). In the composition P and G are commingled to form, at least in part, a PG molecular complex, and the weight ratio of G:P in the composition is at least 0.05:1. In some embodiments, the composition further contains a dispersing agent ("M"). In the composition, P, G, and M are commingled to form a PGM complex. The weight ratio of M:P is from about 0.1:1 to about 2:1, or in some embodiments from about 0.3:1 to about 1:1. In some embodiments, the composition further contains an ionic surfactant present at from 1% to 10% by weight of the composition. In some embodiments, the composition is in the form of spheroidal microparticles having a diameter in the range of about 1-2 microns or less. The microparticles contain phytosterol-glycerine complexes organized at least in part into a liquid crystalline structure.

Another aspect of the invention is a method of producing a composition containing PG complexes. The method includes the steps of: (a) mixing one part by weight of P and at least about 0.05 parts by weight of G, and (b) heating the mixture, whereby a PG molecular complex is formed. Upon cooling, PG complexes are formed, which can be dispersed into an aqueous medium in the form of small microparticles having a diameter of less than 5 microns, and preferably 1-2 microns or less. In some embodiments of the method, a dispersing agent M is admixed with the heated mixture containing P and G, and PGM complexes are formed. M is added to about 0.1 to about 2 parts by weight, based on the weight of P. The addition of the dispersing agent improves the dispersibility in aqueous media of PGM complexes in the form of small microparticles of less than 5 microns, and preferably 1-2 microns or less.

Another aspect of the invention is a beverage or food product containing the PG or PGM complexes described above in the form of a suspension of microparticles. The compositions of the invention are preferably edible compositions that are suitable for use as foods, beverages, or dietary or nutritional supplements, or suitable for addition to foods, food products, beverages, dietary or nutritional supplements for humans or animals. Preferably the edible compositions contain only substances that are recognized as foods, food additives, dietary supplements, or substances that are generally recognized as safe (GRAS) by the U.S. Food and Drug Administration (FDA).

Yet another aspect of the invention is a method of using a beverages, food product, or nutritional supplement to treat or prevent hypercholesterolemia. The method includes administration of the phytosterol- and glycerin-containing PG or PGM complexes described above to a subject in need of reducing their plasma cholesterol levels. The complexes are administered in an amount effective to bind cholesterol in the gastrointestinal tract and prevent or reduce its uptake, thereby reducing LDL and total plasma cholesterol (TC) levels in the subject. In some embodiments of the method, the ratio of LDL to HDL cholesterol of the subject is also reduced.

The compositions and methods of the invention utilize glycerine to inhibit the commonly occurring crystallization of non-esterified phytosterols. The resulting complexes form microparticles that contain liquid crystalline structure and are very small in size, such as in the micron range and submicron range. Their size is greatly reduced, at least ten- to twentyfold, compared to previous forms of phytosterols, and they have excellent dispersibility in water and aqueous media, such as beverages, foods, and nutritional supplements. The microparticles have a diameter of approximately 1-2 microns or smaller, offering a thousand-fold decrease in individual microparticle mass compared to previous forms of phytosterols, a dramatic increase in surface area-to volume ratio, and a corresponding increase in bioavailability and efficacy for blocking cholesterol uptake in the gastrointestinal tract. Accordingly, glycerine complexes of phytosterols, with optional addition of emulsifier, greatly enhance the dispersal of phytosterols by promoting the formation of small liquid crystalline microparticles, that can be stably dispersed in beverages and water-containing foods.

DETAILED DESCRIPTION OF THE INVENTION

Figure 1:
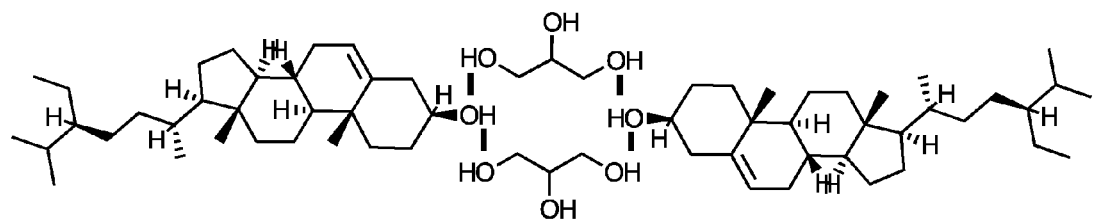
FIG. 1 shows a model of a binary complex (1:1 molar ratio) of a phytosterol and glycerine.

The present invention provides new and advantageous compositions and methods for improving the dispersal and bioavailability of non-esterified phytosterols for use in beverages, foods and dietary supplements. The compositions include molecular complexes formed between phytosterol and glycerine molecules, with the optional addition of one or more dispersing agents such as emulsifiers. The complexes form generally round-shaped, liquid crystalline microparticles of small size, in the micron and sub-micron range, which can be stably dispersed in aqueous media including foods, beverages, and nutritional supplements that can be administered to a human or animal subject to either reduce or enhance the uptake of cholesterol in the gastrointestinal system, depending on the phytosterol composition of the microparticles.

The phytosterols used in compositions of the invention can be any type of non-esterified phytosterol. An intended use of the compositions is to reduce cholesterol uptake in a human or animal subject. As used herein, the term "phytosterol" refers collectively to both phytosterols and phytostanols. Phytosterols for use in the invention are preferably non-esterified. Examples of suitable phytosterols include beta-sitosterol, beta-sitostanol, campesterol, campestanol, stigmasterol, stigmastanol, bras sicasterol, bras sicastanol, clionasterol and clionastanol, and combinations thereof. Suitable phytosterols can be derived, for example, from vegetable oil, tall oil, or a combination thereof. The phytosterols can be hydrated, hemi-hydrated, dehydrated, or a combination thereof.

The methods of the invention include combining, commingling, or complexing glycerine, which is an edible, polar, three-carbon polyol, with phytosterol to alter the crystallization and dispersal properties of the phytosterols and form new molecular complexes of phytosterol with glycerine. In these methods, the glycerine appears to function neither as a solvent nor an emulsifier, but rather as a hydrogen-bonding, complex-forming agent that acts as a physical "spacer" molecule between neighboring phytosterol molecules. In addition to forming a new type of molecular complex, the addition of glycerine alters the physical and chemical associations among groups of phytosterol molecules, thereby preventing their aggregation or crystallization. This alteration is evidenced by a transformation from the crystalline state of the free phytosterol to the liquid crystalline state of the phytosterol-glycerine complex. The ability of glycerine, a hydrophilic molecule, to complex with and at least partially separate phytosterol molecules is surprising and unexpected. The formation of hydrogen bonds that link glycerine and phytosterols in the formed molecular complex may explain the more fluid, yet ordered, structure that characterizes the liquid crystalline phytosterol-glycerine complex.

While the phytosterol-glycerine complex of the invention can be dispersed in an aqueous environment, in certain embodiments an emulsifier such as a monoglyceride or a modified lecithin is added to the phytosterol-glycerine binary complex to increase aqueous dispersal of the complex. As used herein, "free phytosterol" refers to uncomplexed (usually crystalline) phytosterol, "binary complex" refers to a molecular complex of phytosterol in association with glycerine, and "ternary complex" refers to phytosterol in association with glycerine and an emulsifier. The term "phytosterol complex" as used herein refers to the binary and/or ternary complex. Both the binary and ternary complexes may be present in the form of microparticles, such as a suspension of microparticles in an aqueous medium. An "aqueous medium" as used herein can be water or an aqueous solution or suspension containing any desired solutes, such as salts, sugars, or chemicals suitable for use in a food, beverage, or nutritional supplement, or colloid particles such as micelles, proteins, aggregates, or fat droplets.

Improved dispersal of the binary or ternary complexes is evidenced by formation of micron-sized and submicron-sized microparticles, which can be useful to disperse the complexes in water, beverages, liquid formula diets, and water-containing food products. The size (mean diameter) of the binary or ternary complexes can be, for example, less than 5 microns, approximately 4 microns, approximately 2 microns, approximately 1 micron, about 4 microns or less, about 2 microns or less, about 1 micron or less, about 0.5 microns or less, or about 0.3 microns or less. In certain embodiments, the mean diameter of a population of PG or PGM microparticles can be about 1 to about 4 microns, about 2 to about 4 microns, about 1 to about 2 microns, about 0.5 to about 1.0 microns, about 0.2 to about 0.5 microns, or about 0.1 to about 0.2 microns. Several known methods are available for determining the size of the individual microparticles, or size distribution of a population of the microparticles, including microscopy, light scattering, and size exclusion chromatography. The particles generally appear in the light microscope as approximately spherical or spheroidal in shape. The small size of the microparticles is important for ensuring that they remain stably dispersed. The stably dispersed microparticles can remain suspended in an aqueous medium for minutes, hours, or even days to weeks without settling out or floating, depending on the properties of the medium, such as viscosity and specific gravity. Even after some settling has occurred, the microparticles can be readily re-dispersed by agitation of the suspension.

Either the binary or tertiary complexes can also be formulated as dietary supplements including pills, capsules or suspensions. The presence of emulsifier in such dietary supplements assures rapid dispersal of phytosterol complexes in the gastrointestinal (GI) tract after ingestion of a composition containing the complexes. It is generally accepted that, for a given phytosterol preparation, smaller particles that have greater surface area on a gram for gram basis are more "bioavailable" and thus more clinically effective, than larger particles for mixing with, binding, and eliminating cholesterol from the GI tract. The elimination of both dietary cholesterol, i.e., ingested cholesterol, as well as endogenously synthesized cholesterol, results in a beneficial reduction in the level of undesirable plasma cholesterols including LDL-cholesterol. It can be appreciated that various edible ingredients including mono- and diglycerides, lecithins, fats, and any number of other cooperative agents that assist in the binding, emulsification, and dispersal of phytosterols with cholesterol, may be combined in phytosterol formulations to further improve phytosterol bioavailability.

A method of making a phytosterol-glycerine binary complex according to the invention includes combining glycerine with one or more phytosterols to form a binary liquid crystalline complex. The method can include heating, melting, and/or mixing in a blend the following components or compositions comprising them:

(a) at least one non-esterified phytosterol and/or phytostanol (abbreviated "P"); and
(b) glycerine (abbreviated "G").

Binary complexes of this type are abbreviated PG. Optionally, propylene glycol, another edible three-carbon hydrophilic liquid, also may be included in the blend, and can substitute for all or part of the glycerine. According to the method, the P and G components are mixed or commingled, preferably in a melted or liquid state, using any desired mixing equipment, such as conventional mixers used in the food or chemical industry, blenders, propellers, homogenizers, etc. The step of mixing or commingling should provide sufficient mixing action and be carried out for sufficient time to permit molecular complexes to be formed between the phytosterol and the glycerine. The step of mixing or commingling can be carried out at a sufficiently high temperature (e.g., 70° C. or more, or 100° C. or more) to maintain the phytosterol in a melted (liquid) state but also to encourage any water of hydration to dissociate from the phytosterol component and be removed by evaporation or boiling. The final weight ratio of the mixed components G:P is at least 0.5 to 1 (0.5:1). Preferably, enough glycerin is added so that all of the phytosterol in the composition is complexed as a PG complex having an approximately 1:1 molar ratio of glycerine to phytosterol. In some embodiments, an excess of glycerine is added, such that the molar ratio of glycerine to phytosterol is greater than about 1:1.

In another method according to the invention, a ternary phytosterol-glycerine-emulsifier complex is prepared by admixing and heating the above binary blend (i.e., (a)+(b)), either at the same time as the phytosterol and glycerine are combined, or subsequently, with the following dispersing agent component or a composition comprising it:

(c) at least one dispersing agent (abbreviated "M"), such as a monoglyceride (e.g., glyceryl monopalmitate or glyceryl monostearate), a diacylglyceride, a lecithin such as a modified lecithin (e.g., hydrolyzed sunflower lecithin), an ionic surfactant, or a combination thereof. As used herein, a "dispersing agent" is a chemical agent, such as emulsifier or surfactant, that increases the dispersal of phytosterol complexes in an aqueous medium above the level that occurs in the absence of the dispersing agent. Preferred dispersing agents are emulsifiers. Dispersing agent M preferably is added to the mixture of G and P to give a final amount of about 0.1 to about 2.0 parts by weight based on the weight of P. Addition of a dispersing agent to PG complexes forms ternary complexes (abbreviated "PGM"). Examples of suitable dispersing agents include monoglycerides (e.g., glyceryl monopalmitate, glyceryl monostearate, and combinations thereof), lecithins (e.g., hydrolyzed sunflower lecithin, or another hydrolyzed or hydroxylated lecithin), and triglyceride-based oils or fats. In certain embodiments a non-ionic emulsifier is combined with from about 1% to about 10% by weight (based on the total weight of M) of an ionic surfactant. Examples of suitable ionic surfactants include a salt of a fatty acid, wherein the fatty acid is selected from the group consisting of stearic acid, palmitic acid, myristic acid, lauric acid, capric acid, caprylic acid, oleic acid, and combinations thereof. A preferred dispersing agent is the combination of one or more monoglycerides with 5 weight % of sodium stearate. Another preferred dispersing agent contains a modified (e.g., hydrolyzed) lecithin and an ionic surfactant, such as sodium stearate. Ternary PGM complexes are generally more highly dispersible in an aqueous medium than corresponding binary PG complexes.

Both binary and ternary complexes possess a liquid crystalline structure and a very small microparticle size (typically 1-2 microns or less) in aqueous dispersions. Such dispersions differ markedly in their dispersal properties from those prepared with more conventionally crystallized microparticles (typically 10-50 microns) obtained by a process of melting and co-crystallizing phytosterols and monoglycerides in the absence of glycerine.

In addition to being supplied as an aqueous dispersion, the phytosterol complexes can be supplied in the form of a paste, as granules, or as a powder, any of which can be added to a food, food item or food product, liquid food additive, beverage, nutritional beverage, or nutritional or dietary supplement either during formulation of a commercial product or by the end user. Examples of suitable nutritional beverages include cow's milk, sheep's milk, goat's milk, soymilk, almond milk, and coconut milk. Examples of suitable food items include yogurt, cottage cheese, sour cream, soup, salad dressing, tomato catsup, mustard, barbecue sauce, steak sauce, Worcestershire sauce, cocktail sauce, tartar sauce, pickle relish, tomato-based pasta sauce, pizza sauce, prepared chili, and dessert sauce.

The very small average diameter of PG and PGM liquid crystalline microparticles, such as PGM microparticles formed with monoglycerides and/or lecithins, allows these microparticles to remain dispersed in beverages or liquid foods almost indefinitely without settling, while helping to maximize their bioavailability for binding cholesterol. The use of a monoglyceride in forming a ternary PGM complex is preferred, because on a gram-for-gram basis monoglycerides provide more efficient dispersal over the use of fat (i.e., triglycerides) for dispersing phytosterols. While fat has been effectively used for phytosterol dispersal (e.g., forming a "TRP" complex as described in U.S. Pat. No. 7,144,595), human digestion of fat, i.e., triglyceride molecules, yields sn-2 monoglycerides by the action of pancreatic lipase enzymes in the GI tract. Accordingly, monoglycerides are actually much more effective on a weight basis as dispersing agents for phytosterols than fat. Further, supplying one part by weight of monoglycerides in the presently described PGM complex is expected to provide the equivalent dispersing activity (with only ⅓ the calories) of up to a three parts by weight of fat.

A useful PGM complex may be formulated, for example, by heating and melting together approximately 1 part by weight non-esterified phytosterols with 0.5 part by weight glycerine and approximately 0.5 to 2 parts by weight (e.g., 1 part by weight) of a monoglyceride emulsifier, such as Myvatex 8-60 manufactured by Kerry Ingredients and Flavours, Beloit, Wis. The latter contains glyceryl monostearate, glyceryl monopalmitate and a small amount (i.e., 4-6% by weight) of sodium stearate. This exemplary PGM complex formula contains approximately 40% by weight of phytosterols. Formulations containing higher or lower proportions of glycerine and emulsifier relative to phytosterols may also be constituted. The melting temperatures of typical PGM complexes tend to be conveniently reduced (e.g., 60-90° C.) when compared with pure phytosterols (e.g., 135-140° C.) owing to the presence of lower melting point emulsifiers such as a fatty acid monoglycerides.

In summary, a highly dispersible liquid crystalline PGM complex can be made by heating and melting together non-esterified phytosterols, glycerine, and an emulsifier such as a monoglyceride, a lecithin, or another dispersing agent. Such PGM complexes are up to 100% dispersible in aqueous media and can be incorporated into beverages and foods by blending, used to make a liquid concentrate for addition to such foods and beverages, or formulated as dietary supplements, including pills, capsules, and liquid dietary supplements. The resulting liquid crystalline PGM dispersions contain microparticles of a small size in the micron to sub-micron range, which is believed to represent the smallest particle size distribution of any edible phytosterol composition reported prior to the invention.

The Phytosterol-Glycerine Complex

Glycerine (also known as glycerin, glycerol, or $C_3H_8O_3$) is a relatively low molecular weight (MW=92) water-soluble, polar compound which is liquid at room temperature and has low vapor pressure. It is a colorless, odorless, edible, sweet-tasting hygroscopic liquid that is widely used in pharmaceutical preparations and foods. Glycerine is generally recognized as safe (GRAS) for use in foods, and is categorized by the FDA and the American Dietetic Association as a carbohydrate sweetener. It is produced by many companies as a by-product of making soap, biodiesel fuels and refining edible fats and oils. Its three hydroxyl groups are responsible for its water-miscibility and hygroscopic nature. Glycerine is a precursor for synthesis of triglycerides and of phospholipids in the liver and adipose tissue. When the body uses stored fat as a source of energy, glycerine and fatty acids are released into the bloodstream. Nutritionally, glycerine is a carbohydrate that can be enzymatically converted into glucose by the liver to provide energy for cellular metabolism. Before glycerine can enter the pathway of glycolysis or gluconeogenesis, it must be converted enzymatically to the intermediate, glyceraldehyde 3-phosphate. Glycerine is known to protect lipid membranes in cells, and may prevent damage due to osmotic stress and dehydration. Glycerine is also well known as a moisturizer or humectant for human skin. In view of these properties, it was surprising to find that glycerine can form an intimate complex with the hydrophobic and usually crystalline phytosterols.

The invention provides an associative chemical complex formed by combining glycerine, an edible liquid, with melted phytosterols and commingling the melted mixture to form the complex. This complex is believed to result from intermolecular hydrogen bonding of one or more of the hydroxyl groups found in glycerine with the single hydroxyl group found in the phytosterol molecule. The complex fails to crystallize as traditional phytosterol crystals (e.g., needles, rods, or plates); instead, the complex disperses the phytosterol material in aqueous media (e.g., water, beverages, water-based foods, controlled nutritional beverages, dietary supplements, saline, cell culture media, or aquaculture media). Formation of the readily dispersed PG or PGM complexes also facilitates chemical mixing and association of phytosterol molecules with cholesterol molecules in the GI tract following phytosterol ingestion.

Non-esterified phytosterol (i.e., free phytosterol) preparations used herein are purified, food grade materials typically containing in excess of 90% free phytosterols. The phytosterol compositions may include varying proportions of beta-sitosterol, campesterol, stigmasterol and brassicasterol as well as reduced or hydrogenated chemical forms known as stanols. Suitable commercial sources for free phytosterols include Vegapure® FS (Cognis Corp., La Grange, Ill.), CardioAid™ non-esterified phytosterols from soybeans (Archer Daniels Midland, Inc., Decatur, Ill., also known as ADM, Inc.) and CoroWise®.

Non-esterified phytosterols routinely exist as monohydrated molecules but can also exist as hemi-hydrated and anhydrous forms depending upon the temperature and the surrounding chemical environment. Upon heating in a fat or in glycerine to a temperature above the boiling point of water, a suspension of crystalline phytosterol powder is observed to boil briefly as the phytosterol monohydrate becomes anhydrous and water molecules are evolved as steam. With such heating in the presence of glycerine, it is believed that a glycerine molecule replaces the water molecule previously hydrogen-bonded to the hydroxyl moiety of the phytosterol molecule, with a hydrogen bonding interaction between a hydroxyl group on glycerine and the phytosterol hydroxyl. In the process, the phytosterol becomes either fully or partially dehydrated. Upon cooling, the glycerine-sterol complex forms amorphous (i.e., not a regular crystalline solid) microspherules that further examination has shown to contain liquid crystalline material rather than conventional rigid crystals. The glycerine-complexed phytosterol molecules still cohere with one another about as strongly as the original phytosterol monohydrate molecules, evidenced by maintenance of an elevated melting point (in excess of 130° C.). However, as described below, the presence of glycerine in the liquid crystalline phytosterol binary complex structure predisposes this structure to enhanced disruption by water after emulsifiers have also been incorporated into the structure to form a ternary complex structure.

It was discovered that a substantial amount of glycerine can be combined with phytosterol to form a complex (up to approximately 20% glycerine based on the weight of phytosterol). This was surprising given that glycerine is a low molecular weight hydrophilic substance whereas phytosterols (e.g., beta-sitosterol, campesterol and stigmasterol) are highly hydrophobic substances. It was even more surprising given that when a small amount of phytosterol, e.g., 1% by weight, is heated in glycerine to a temperature that exceeded the melting temperature of the phytosterol (e.g., 150° C.), only a negligible amount of the phytosterol dissolves in the glycerine. The question arose, why can 20% glycerine dissolve into melted phytosterols when a small amount of phytosterol will not dissolve into glycerine. It was also difficult to explain why, when glycerine was replaced with propylene glycol, another small hydrophilic liquid, the propylene glycol and phytosterols were found to be substantially miscible at 150° C. For example, equal weight percentages of these ingredients dissolve easily in one another.

The approximate 20% by weight saturation level of glycerine relative to phytosterols represents the formation of a 1:1 molecular stoichiometric complex in which one glycerine molecule forms a hydrogen bond at the hydroxyl group of one phytosterol molecule (glycerine/sterol molecular weights=92/415=22%). This phenomenon differs from chemical solubility in which a solute and solvent are not constrained by formation of such a complex. The amount of glycerine present in such a complex is insufficient for the glycerine to form a bulk liquid phase, and in any event phytosterols are too hydrophobic to dissolve in a polar liquid such as glycerine.

The above-described melted mixtures of phytosterols and glycerine or propylene glycol were cooled to form a solid mass and then investigated by phase contrast light microscopy. With propylene glycol, the phytosterols solidified principally as crystalline particles of approximately 20-200 microns, whereas the glycerine-associated phytosterols solidified as masses of countless microparticles, each measuring approximately 1-2 microns or less in diameter and spherical or spheroidal in shape. The microspheres appeared amorphous (i.e., not a regular crystalline solid) as viewed using phase contrast illumination. With regard to dispersibility, the glycerine-complexed material was far superior to the propylene glycol material.

Polarized light microscopy allows determination of the extent of ordering and alignment of molecules within PG or PGM microparticles. While the overall shape of the microparticles appears round and non-crystalline, their appearance under polarized light confirms that they contained highly oriented molecules characteristic of liquid crystals. Thus, when the above-described glycerine-containing phytosterol samples were placed on a microscope slide and examined at 100×-200× magnification under transmitted polarized light (Olympus Model BX-51 microscope) essentially 100% of the microparticles appeared alternately bright (polarized light-transmitting) and subsequently dark (polarized light-non-transmitting) as samples were progressively rotated on the microscope stage. Therefore, glycerine-complexed phytosterol molecules maintain a physical and optical alignment in spite of the fact that solid phase crystals characteristic of simple phytosterols were not formed during cooling and solidification of the complex. Interestingly, while an elevated temperature allowed the hydrogen-bonded glycerine-sterol material to melt, and to separate into micron-sized microspheres, the phytosterol molecules in the cooled microspheres were highly ordered.

Phase contrast microscopy allows differentiation among particulate structures based upon their external morphology. "Crystals" are identified by their angular appearance (e.g., angular-shaped polygons, plates, rods and needles) and their light refraction. This contrasts with the appearance of "amorphous" or "non-crystalline" particles, which are typically round or globular in shape and appear either dark or exhibiting reduced light refraction. On the other hand, a "mesomorphic" or "liquid crystalline" state, as used herein, refers to a physical state of matter (including multiple intermediate transition states) that is intermediate between a liquid and a fully solid state. The solid state, in the case of substantially pure phytosterols, is typically crystalline. Thus, substances and microparticles formed from such substances, that originally exist in a crystalline state may, because of an alteration in chemical make-up (e.g., combining with glycerine) undergo a transition through one or more intermediate so-called liquid crystalline or mesophase states. During this transition, mesomorphic substances may melt and begin to flow, assuming rounded shapes characteristic of liquids rather than solids, even though the substances may retain some crystalline properties. For the purposes herein, such mesophases or liquid crystalline states for phytosterol-containing particles and microparticles are termed "amorphous" or "liquid" materials (as opposed to solid or crystalline materials) provided that they are fluid. Fluidity is shown for these materials when they form generally round microparticles rather than optically refracting angular solid particles. Such fluidity is functionally important because it allows formation of very small microparticles and thus large surface areas that favor increased phytosterol bioavailability.

The addition of glycerine to phytosterol, and the consequent formation of a phytosterol-glycerine complex, is very useful because the complex forms very small microparticles whose ratio of surface area to mass is very great. The tendency of these microparticles to aggregate can be opposed either by mixing to apply a shear force using conventional dairy homogenization equipment, high shear blade blending, propeller mixers and the like, or through the addition of emulsifiers. Addition of an emulsifier to the phytosterol-glycerine melt causes the microparticles to disaggregate into individual microparticles. Since the microparticles offer a vary small diameter and maximized surface area, they produce dispersions that remain stably suspended in aqueous media, such as beverages, for long periods of time without settling. A further advantage of the microparticulate form of PG and PGM complexes is their high degree of bioavailability.

Hydrogen Bonding in Phytosterol-Glycerine Complexes

The chemical interaction between phytosterol molecules and glycerine in PG and PGM complexes of the invention are believed to involve a 1:1 molecular complex formed by hydrogen bonding between glycerine and phytosterol molecules. The expected molecular associations are shown diagrammatically in FIGS. 1 and 2, depicting beta-sitosterol and glycerine molecules. These complexed molecules can form ordered structures in which phytosterol molecules align parallel to one another. In a hydrophobic environment, the pairwise complex shown in FIG. 1 may be favored, since this arrangement locates the hydrophilic glycerine molecules oriented inward. Thus, in a heated anhydrous mixture containing mobile beta-sitosterol and glycerine molecules, the hydrophobic phytosterol molecules are expected to self-associate, and the glycerine molecules should likewise self-associate as their free hydroxyl groups form hydrogen bonds with one another. By contrast, in an aqueous environment, most glycerine molecules should be oriented outward to maximize hydrogen bonding with water (FIG. 2). While not intending to limit the invention to any particular structure of the phytosterol complexes or molecular bonding arrangement, it is believed that the planar phytosterol ring structures are stacked into parallel arrays as indicated in FIG. 2.

Hydrogen bonding between glycerine and the hydroxyl group of the phytosterol molecule weakens or disrupts the hydrophobic interactions that give rise to normal crystallization following melting and cooling of either a single molecular species (e.g., beta-sitosterol) or mixed species (e.g., soybean oil-derived phytosterols). This results in the formation of a non-crystalline solid when a molten mixture of glycerine and phytosterols is cooled to room temperature. While not intending to limit the invention to any particular mechanism or molecular structure, it is believed that two glycerine molecules forming a double bridge between two neighboring beta-sitosterol molecules would produce a 1:1 stoichiometric molecular complex, as depicted in FIG. 1. Based on their molecular weights, 92g of glycerine would combine with 415g beta-sitosterol. This would correspond to a weight ratio of 22 parts glycerine to 100 parts phytosterol, and it is consistent with the observation that somewhat more than 20 parts by weight of glycerine are able to dissolve during mixing with molten phytosterols. Between 20 and 30 parts by weight were observed to prevent crystallization of 100 parts by weight of phytosterols.

Figure 2:
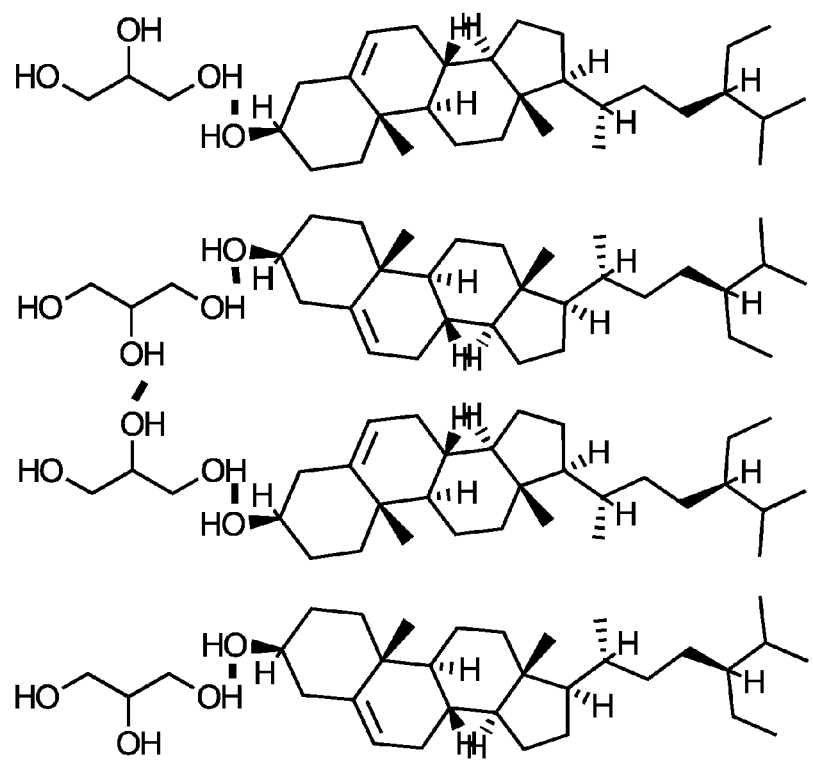
FIG. 2 shows a model of binary complexes of a phytosterol and glycerine with alignment of the phytosterol molecules.

With regard to the third hydroxyl group in the glycerine molecule that is not believed to participate in the hydrogen bonding structure shown in FIG. 1, it would be available for hydrogen bonding with a polar molecule, e.g., water, or an emulsifier. This can occur when other ingredients are mixed together with the binary phytosterol complex in a food or beverage composition. By contrast, as shown in FIG. 2, in an aqueous environment two of the three glycerine hydroxyl groups are available for assisting in dispersal of the phytosterol molecule. Thus, the glycerine molecule, when hydrogen bonded to a phytosterol molecule, may increase the density of chemically available hydroxyl groups from one (the original phytosterol hydroxyl group) to at least two.

It is interesting to compare and contrast the role of glycerine with the role of an emulsifier in terms of chemical interaction with phytosterol molecules. An emulsifier molecule must generally be of sufficient size to be amphiphilic. That is, the emulsifier molecule should contain at least one "water-associating" or hydrophilic portion, and at least one "fat-associating" or hydrophobic portion. These two different portions allow the combining of liquids that normally do not mix, such as fat and water. Thus, lecithin from egg yolk is amphiphilic and can stabilize fat microdroplets suspended, for example, within a continuous "external" phase of aqueous vinegar and other flavorings to create the emulsion recognized as mayonnaise. While varying amounts of emulsifiers may be added for stabilizing such emulsions, there are typically no "solubility limits" per se with the use of an emulsifier because the emulsifier occupies a separate interface position in a liquid system between two components that do not dissolve in one another, e.g., oil and water. By comparison, glycerine is a small three carbon-containing molecule that is either immiscible or miscible to varying degrees in other solvents. By conventional definitions, glycerine is a solvent or co-solvent rather than an emulsifier. When mixed with phytosterols that have been melted at a temperature of approximately 135° C., glycerine reaches what appears to be a solubility limit (i.e., saturation level) at about 25g per 100g phytosterols. Such solubility limits are commonly encountered among solvents and co-solvents. For example, alcohol molecules whose molecular structures contains more than three carbon atoms reach defined solubility limits in water, e.g., n-butanol @ 9.1 ml per 100 ml water, n-amyl alcohol @ 2.7 g per 100g water. However, in the present invention glycerine acts to alter the crystal form of phytosterols rather than as a solvent or as an emulsifying agent.

Dispersing Agents

The binary complex formed between glycerine and phytosterols can be modified to form a more highly water-dispersible ternary complex by further adding a dispersing agent to the heated blend of melted phytosterol and glycerine. A variety of emulsifiers have been shown to be capable of dispersing the phytosterol-glycerine complexes in water or other aqueous media. For example, monoglycerides such as glyceryl monostearate or glyceryl monopalmitate, or modified lecitihns can be used as the dispersing agent. Monoglycerides are preferred over other emulsifiers because they contain fatty acids that enhance the bioavailability of non-esterified phytosterols (see Perlman et al., U.S. Pat. No. 6,638,547). Since fat molecules (triglycerides) are converted by lipase enzymes to monoglycerides during digestion, it is likely that monoglycerides also act as the biologically active dispersing agent when fats are used as a phytosterol carrier vehicle and combined with foods.

Ternary molecular complexes containing monoglycerides commingled with PG complexes can be easily produced by admixing and melting all of the ingredients (sterol, glycerine, and emulsifier) together and cooling them. Alternatively, the ternary blend can be made in successive steps by first making a PG complex and then admixing the monoglyceride. The result is a plastic-like ternary solid, which like the binary PG solid, appears amorphous rather than crystalline when examined by phase contrast microscopy. However, polarized light microscopy shows that the ternary complex, like the binary complex, forms a liquid crystalline molecular structure. The preponderance of liquid crystalline material was observed by rotating specimens of these complexed materials on glass slides supported on the microscope stage during transmission of cross-polarized light. As the specimen is rotated, localized portions of the material (including individual micro-spherules) visually transition between bright and dark as the polarized light is alternately transmitted and not transmitted through the liquid crystalline material. By direct visual examination, the liquid crystalline state of glycerine-containing phytosterol material supports formation of ultra-small fluid microparticles. The complexes are fully and relatively easily dispersible in water and other aqueous liquids (e.g., cows milk and soymilk) as well as aqueous foods, in the form of tiny micron and sub-micron-sized spherules ($\leqq 2$ μm or $\leqq 1$ μm in diameter).

The presence of glycerine in a binary complex blocks the crystallization of phytosterol, and in a ternary complex with phytosterol and a dispersing agent such as a monoglyceride blocks co-crystallization that otherwise occurs when these constituents are melted together and cooled. When unaltered by glycerine, the latter binary complex of phytosterols and monoglyceride (a PM complex) crystallizes quickly, as can be viewed by phase contrast microscopy, and produces a less stable and less useful suspension of larger crystalline microparticles in water (20-100 microns in diameter). Such crystals have poor bioavailability. Smaller fluid (non-crystalline) microparticles have the advantage of providing a much greater surface area for a given amount of material than larger particles. Therefore, the smaller amorphous glycerine-containing ternary phytosterol microparticles will have superior bioavailability for combining with and binding cholesterol than the larger binary crystalline PM particles formed without glycerine. With the advantage of greater cholesterol binding, the smaller phytosterol-containing microparticles formed with the benefit of glycerine are expected to increase fecal elimination of cholesterol from the GI tract and thereby further decrease mammalian plasma LDL cholesterol levels.

In addition to inhibiting the crystallization of phytosterols, glycerine appears to modify the chemistry of monoglyceride emulsifiers and their formation of complexes with phytosterols. The interaction between glycerine and monoglycerides may beneficially inhibit the formation of larger binary crystals that are otherwise formed when monoglycerides such as glyceryl monostearate co-crystallize with phytosterols. Instead, an amorphous and physically plastic ternary mixture is formed, that includes glycerine, phytosterols (including beta-sitosterol for example) and at least one amphiphilic dispersing agent or emulsifier, such as a monoglyceride (e.g., glyceryl monostearate). The dispersing agent facilitates dispersal of the ternary mixture as microparticulate spherules in any aqueous medium. Upon dispersal in water, for example, the spherules containing glycerine-modified phytosterols and emulsifier appear to be smaller than other commercially available phytosterol particles. The average diameter of these microparticles is many-fold smaller than crystalline microparticles formed without the benefit of glycerine. As a result of their smaller size, PGM microparticles (e.g., containing glycerine-phytosterol-monoglyceride) are expected to have improved bioavailability when ingested, compared to either unmodified PM particles (e.g., phytosterol-monoglyceride) that share the same combination of phytosterols and monoglyceride emulsifiers but are formulated without the benefit of glycerine. Accordingly, PGM microparticles are expected to bind increased levels of cholesterol in the digestive system, promoting greater fecal elimination of cholesterol, thereby further reducing plasma LDL cholesterol levels.

Emulsifiers are amphiphilic agents that enable the dispersal of phytosterol-glycerine complexes in aqueous media and a diversity of water-containing edible materials. Examples of suitable emulsifiers include edible non-ionic and ionic surfactants, e.g., mono- and diglycerides, unmodified and modified lecithins (e.g., hydrolyzed and hydroxylated lecithins), and synthetic emulsifiers such as acetic, lactic, citric, and succinic acid esters of monoglycerides, diacetyl tartaric acid ester of mono- and diglycerides (DATEM), polyglycerol esters of fatty acids, sorbitan esters of fatty acids and sucrose esters of fatty acids, edible salts of fatty acids, and combinations of these. One example of a useful monoglyceride emulsifier is a combination of glyceryl monostearate and glyceryl monopalmitate derived from palm oil; this is available as Myvatex 8-60, manufactured by Kerry Ingredients and Flavours (Beloit, Wis.).

An unmodified lecithin that has a low solubility in water may be combined with a modified lecithin or other emulsifier(s) to form a mixed amphiphilic emulsifier. Lecithins used herein are preferably modified such that they are more hydrophilic relative to unmodified lecithins. In some embodiments, a natural vegetable lecithin is modified by either hydroxylation or hydrolysis (e.g., modified sunflower lecithin), rendering the lecithin sufficiently hydrophilic so that when combined with a preformed PG complex, the resultant amphiphilic particles are dispersible in water-containing liquids (e.g., cow's milk or soymilk).

When considering emulsifiers, it may be useful to consider their hydrophilic-lipophilic balance (HLB). The HLB value may be calculated based on values for the different regions of the emulsifier molecule. W. C. Griffin's method for classifying non-ionic emulsifiers by their HLB value (J. Soc. Cosmetic Chemists 1:311 (1949)) considered the molecular mass of the hydrophilic portion of a molecule compared to the whole molecule, to provide an HLB number on an arbitrary scale of 0 to 20. A value of 0 corresponds to a fully lipophilic molecule while a value of 20 corresponds to a fully hydrophilic molecule. According to Griffin, the HLB value predicts the surfactant properties of a molecule. More specifically, a value from 4 to 6 indicates a water in oil (w/o) emulsifier while a value from 8 to 18 indicates an oil in water (o/w) emulsifier. In certain embodiments of the invention, emulsifiers are used that emulsify the glycerine-sterol complex into water. In some embodiments, the applicable HLB range is about 8 to about 18. In particular embodiments, lecithins used in the amphiphilic emulsifiers described herein can be modified such that they have an HLB range of about 8 to about 18. In other embodiments, an amphiphilic emulsifier or mixture of amphiphilic emulsifier molecules having both lipophilic and hydrophilic chemical properties can be used. In yet other embodiments, because beverages to be supplemented with the glycerine-sterol complex include cow's milk and soymilk that are often purchased by health-conscious consumers, the emulsifier can be derived from a natural source. For example, lecithin that is prepared directly or indirectly from a natural food source material can be used. In certain embodiments, the emulsifier may include chemically synthesized emulsifiers, such as a sorbitan derivative or a polyethylene glycol.

In one embodiment, the amphiphilic emulsifier includes hydrolyzed sunflower lecithin (Giralec® HE-60 or Giralec® H-US produced by Austrade, Inc., Palm Beach Gardens, Fla.). In some embodiments, from about 90% to about 99% by weight of a preformed phytosterol-glycerine complex is blended with from about 10% to about 1% by weight of a modified lecithin to produce microparticles dispersible in liquids such as beverages and fluid foods. In other embodiments, from about 94% to about 98% by weight of the preformed phytosterol-glycerine complex is blended with from about 8% to about 2% by weight of modified lecithin.

In certain embodiments of dispersing agents, lecithin, or another lipid such as a diacyl glycerol or triacylglycerol, is hydrolyzed using enzymatic phospholipase A rather than acid or base hydrolysis, allowing the beta (sn-2) fatty acid to be selectively removed. In other embodiments, hydroxylation of lecithin or another lipid is performed by reacting lecithin with hydrogen peroxide and lactic or acetic acid. In particular embodiments, hydroxyl groups are added at sites of unsaturation in the lecithin's fatty acids.

Modified lecithins used as dispersants in the present invention include: Yelkin®1018 soy lecithin (hydroxylated) with an HLB of 9 (ADM, Inc.); Alcolec® C LPC20 canola lecithin (enzyme-hydrolyzed) with an HLB of 12 (American Lecithin Company (ALC, Inc.), Oxford, Conn.); Alcolec® EM soy lecithin (enzyme-hydrolyzed) with an HLB of 9 (ALC); and Giralec®HE-60 sunflower lecithin (enzyme-hydrolyzed) with an HLB of 8-9 (Austrade, Inc., Palm Beach Gardens, Fla.). In certain embodiments, modified lecithins certified as produced from natural non-genetically modified organisms can be used.

Sterol-glycerine complexes were found to be uniformly and stably dispersed throughout a liquid aqueous medium using modified (e.g., hydrolyzed or hydroxylated) lecithins having HLB values of between about 8 and about 12 that are typical for emulsifiers of oil in water. Natural (unmodified) lecithins may not be sufficiently active in some cases to achieve the desired uniform and stable dispersal. As used herein, stable dispersal of PG or PGM microparticles means that the particles do not separate (float or sink) from the liquid to which they are added, that is, to the extent that they can't be re-dispersed with shaking.

As utilized and defined in the presently described formulations, monoglycerides are dispersing agents or emulsifiers, but glycerine (or propylene glycol) is not a dispersing agent or emulsifier. This differentiation is based on chemical and molecular affinities, and the fact that the monoglyceride molecule includes both a hydrophobic fatty acid moiety and two hydrophilic hydroxyl groups that enable this amphiphilic emulsifier molecule to bind and combine with both hydrophobic phytosterol molecules and water. Glycerine, however, contains three hydroxyl groups and is miscible with water, and is believed to interact with phytosterols through hydrogen bonding as explained above. Accordingly, glycerine appears to act neither as an emulsifier or dispersing agent nor as a solvent in forming a complex with phytosterols.

In addition to forming a complex when combined with melted phytosterols, glycerine exhibits partial solubility in melted monoglycerides. Thus for example, combining (in the absence of water) 10% by weight glycerine with the commercial Myvatex 8-60 monoglyceride product, results in a significant decrease (6-8° C.) in the 70° C. melting point of the monoglyceride. This melting point depression is consistent with the physical chemistry of a crystalline solid whose structure is interrupted by a solute molecule. In this case, glycerine, as a solute molecule may interact with a monoglyceride, thereby decreasing the monoglyceride melting point. Larger amounts of glycerine (e.g., 30-50% or more by weight) combined with the same monoglycerides induce a different change, i.e., the prevention of crystallization and promotion of gel formation.

Co-crystallizing complexes of phytosterols and monoglycerides is described by Akashe, et al. in U.S. Pat. No. 6,267,963. Such complexes formed between emulsifiers and phytosterols have substantially lower melting temperatures than phytosterols alone (see Example 2 in U.S. Pat. No. 6,267,963). By contrast, when a PG complex containing a 1:1 weight ratio of glycerine (with or without propylene glycol) and phytosterols (soybean or tall oil-derived phytosterols) is heated, melted and cooled to room temperature, the re-melting temperature (128-130° C.) is only slightly lower than that of the original phytosterols (approximately 132-134° C.). This finding suggests that the chemical complex formed between glycerine and phytosterol may be relatively weak. Thus, glycerine appears to interact uniquely with non-esterified phytosterols on the one hand, causing conversion to a liquid crystalline state, and with monoglycerides on the other hand to retard their crystallization and induce a gel-like state. When combined in a ternary complex of glycerine, phytoterols and monoglyceride, a highly dispersible product is created having both liquid crystalline and amorphous characteristics.

As described above, the addition of glycerine and its proposed complex formation with phytosterols has a very limited effect on the solidification temperature and melting point of the phytosterols in spite of the fact that phytosterol crystallization is altered from hard crystal to liquid crystal formation. This observation suggests that the thermodynamic stability of the liquid crystalline glycerine-phytosterol solid complex is comparable to that of traditionally crystallized phytosterol monohydrate. On the other hand, judging from the effect of glycerine on the melting point of monoglycerides, glycerine causes a greater disruption of the crystalline structure and stability of monoglycerides. Thus, when 80% by weight of a monoglyceride-based emulsifier (Myvatex 8-60, Kerry Ingredients, Beloit, Wis.) that originally melts at a temperature of approximately 70° C. is mixed with 20% by weight glycerine, the mixture melts and also begins to re-crystallize at approximately 68° C. As the proportion of glycerine is increased to approximately 35% by weight, and the monoglyceride is decreased to 65% by weight, crystallization and melting occur at a significantly lower temperature, i.e., 62-63° C. rather than 70° C. This significant 7-8° C. decrease in the monoglyceride melting temperature suggests both chemical dilution and de-stabilization of the crystalline monoglyceride structure by glycerine. Moreover, while a 60% monoglyceride+40% glycerine melt is clear and fluid above 95-100° C., at lower temperatures (63°-95 C) a clear gel-like phase forms between the glycerine and the monoglyceride before crystallization commences at a temperature of 62-63° C. This glycerine-induced alteration of monoglyceride crystallization explains the observation that glycerine also inhibits regular co-crystallization of monoglycerides with phytosterols when they are all mixed together and melted.

When a 1:1:1 mixture or a 0.5:1:1 mixture of glycerine, free phytosterols (FG-50 from Cargill, Inc., Minneapolis, Minn.), and monoglycerides (e.g., Myvatex 8-60 containing approximately equal amounts of glyceryl monopalmitate and glyceryl monostearate) is heated, melted, and cooled, the glycerine substantially interferes with the phytosterols and monoglycerides forming conventional crystalline solids. Instead, a liquid crystalline complex is formed. As a beneficial result, the cooled liquid crystalline solids are readily dispersible in water and aqueous beverages such as milk. Thus, glycerine not only produces a novel binary complex with phytosterols, but also forms a novel ternary complex that includes glycerine, phytosterols, and monoglyceride molecules.

The ratio of glycerine, phytosterol, and monoglyceride components of a PGM ternary composition containing monoglycerides as the dispersing agent can vary depending on the relative amounts of phytosterol and monoglyceride. The ratio of G to P, as for all phytosterol complexes of the invention, is in the range from about 0.05 g of G per gram of P to about 1 gram of G to 1 gram of P. Similarly, the ratio of M to P is in the range from about 0.1 to about 2.0, based on the weight of P. It is apparent, then, that the relative amounts of G and M can vary depending on how much monoglyceride is used relative to the amount of phytosterol. In a preferred embodiment, the weight ratio of G:P:M is at least about 0.5:1:1, where the amount of G can be 0.5 or greater and the amounts of P and M are each 1. In another preferred embodiment, the weight ratio of G:P:M is about 0.7:1:1. In another preferred embodiment, the weight ratio of G:P:M is about 0.5:1:0.5. In another preferred embodiment, with the weight of P held constant at 1 unit, the relative weights of G and M can be independently varied, each between approximately 0.4 and 1 unit. In yet another preferred embodiment, the weight ratio of G:M is about 0.5 gram of G to about 1 gram of M. In still another preferred embodiment, the molar ratio of G:M is about 2:1.

Dispersal of PG or PGM microparticles in aqueous beverages and foods can be further improved by including a small but effective amount of ionic surfactant in the PGM blend. For example, about 1% to about 5% by weight of sodium stearate can be combined with, and added into another emulsifier. For example, 5% by weight sodium stearate may be combined with 95% by weight of a non-ionic emulsifier such as glyceryl monostearate and glyceryl monopalmitate. In particular with PGM microparticles, where glycerine already acts to prevent crystallization of phytosterols and a dispersing agent such as a monoglyceride further promotes dispersal, addition of an ionic surfactant produces a more uniform emulsion. Better emulsions are expected to provide greater microparticle surface areas, and consequently better dispersal in beverages such as milk and increased binding of both biliary and dietary-derived cholesterol in the gastrointestinal tract. Further, the monoglyceride component with its fatty acid binding to the phytosterol molecule is expected to enhance cholesterol-phytosterol mixed micelle formation in the GI tract. All of these factors contribute to increased phytosterol bioavailability, which is key to increasing the fecal elimination of cholesterol and decreasing the levels of plasma cholesterol.

The kinetics of the dispersal of PGM microparticles is rapid. Their dispersal can be observed to occur rapidly and fully after mixing into either cold or hot aqueous beverages or foods, with the use of only low to moderate shear force or agitation. Stable suspensions and emulsions can be produced either by diluting and shear-mixing a semi-solid PGM concentrate at ambient temperature in water, milk or other fluids, or by heat-softening or even re-melting the PGM complexes and then dispersing them directly into a hot or cold aqueous medium. If desired, the softened or the melted composition can also be dispersed directly into liquid, since the re-melt temperatures of the ternary PGM complexes are below the boiling point of water. As yet another option for dispersal of the PGM material, after forming the PGM complex by melting, mixing and cooling the ingredients, an aqueous concentrate can be made by blending 1 part of the PGM with, for example, 1-2 parts of milk, water or other aqueous liquid. This concentrate can have the consistency of yogurt or sour cream, and can be easily dispersed in a beverage or food product using low shear mixing. It can also be constituted as a gel, or gelled by rapid chilling. In either form, it can serve as an additive or condiment to foods or beverages, such as coffee or tea.

Over a period of days following melt-blending of the PGM mixture, during storage at room temperature, the initially amorphous (non-crystalline) PGM complex may experience some growth of crystals containing phytosterol and monoglyceride. Since this is generally undesirable, and to assure that the PGM when added to a beverage or food is amorphous (with maximum microparticle surface area), the PGM can be remelted before use. Remelting typically can be performed at 80-90° C. After remelting, it is stable for a period of hours to days.

For ease in dispersal, a PGM blend that has been gelled can also be pre-blended with a limited amount of cold or ambient temperature milk, water, or other liquid to form a concentrated aqueous pre-mix. For example, 1 part PGM gel can be mixed with 1-2 parts by weight of water or milk to form a PGM concentrate or pre-mix. Approximately 3.0 g of the above-described PGM blend containing equal parts by weight of free phytosterols, glycerine, and a monoglyceride such as Myvatex 8-60 will provide a bioavailable daily level of more than 800 mg phytosterols as prescribed by the U.S. FDA for achieving a meaningful reduction in plasma cholesterol level and allowing a food product to carry the FDA-approved heart health claim for phytosterols.

Methods of Use

The compositions of the invention can be used to reduce the uptake of sterols, such as cholesterol, in the gastrointestinal tract of a human or animal subject, by including the compositions in solid or liquid food, water, or nutritional or medical products ingested by the subject.

In one such method, a composition containing microparticulate PG or PGM complexes are administered to a subject in order to reduce one or more plasma cholesterol levels in the subject. The subject consumes the phytosterol-glycerine complexes with food or drink, or as a supplement in the form of pills, capsules, powder, or liquid, and in the GI tract the phystosterol binds and sequesters cholesterol present in the GI tract and prevents its uptake into the bloodstream. It is well known that cholesterol can bind to phytosterols and reduce cholesterol uptake. Regular dietary intake of PG and PGM complexes, such as the intake of approximately 1-2 g of phytosterols per day, is known to typically result in a substantial reduction in plasma LDL-cholesterol and total cholesterol (see U.S. Pat. Nos. 7,709,038, 7,575,768, 7,144,595 and 6,638,547. For a human subject, the subject preferably consumes a total of about 0.5 g to about 4.0 g of phytosterols per day. The amount administered can be adjusted in accordance with measurements of the subjects cholesterol levels during the therapy, so as to obtain a desired range of cholesterol levels. A selected amount of PG or PGM complexes is consumed by the subject for a period of time sufficient to achieve the desired reduction in cholesterol levels. Preferably, PG or PGM is administered to the subject on a daily, alternating day, or weekly basis, and administration is continued for one or more weeks, months or years, or indefinitely, The amount of PG or PGM consumed by the subject can also be varied depending on the anticipated amount of cholesterol in the subjects daily diet. The amount of PG or PGM administered to the subject can also be varied according to the actual or anticipated consumption of cholesterol on a meal-by-meal basis.

This method is capable of reducing both total plasma cholesterol and plasma LDL-cholesterol. In some embodiments of the method, the ratio of LDL-cholesterol to HDL-cholesterol is reduced. The method can be used to treat hypercholesterolemia. The method also can be used to prevent hypercholesterolemia by reducing plasma cholesterol levels in a subject suspected of having or acquiring hypercholesterolemia. In this context, prevention of hypercholesterolemia, or aiding in the prevention of hypercholesterolemia, requires only that a reduction of plasma cholesterol levels is achieved in some subjects to whom it is administered and, optionally, that the reduction is maintained with continued administration for a period of time, such as days, weeks, months, or years, so as to reduce the probability of the subject acquiring hypercholesterolemia, or the symptoms resulting therefrom.

EXAMPLES

Example 1

Formation of Phytosterol-Glycerine Compexes

Commercial crystalline phytosterol particles (CoroWise® FG-50 soybean oil-derived phytosterols from the Cargill, Inc., Minneapolis, Minn.) were mixed with an excess of liquid glycerine on a microscope slide. At ambient temperature, little if any interaction between glycerine and crystalline phytosterol particles was observed using phase contrast microscopy at 150× magnification. However, a physical transformation was induced by heating and melting the phytosterol particles suspended in glycerine to approximately 150° C. on a glass microscope slide using a Bunsen burner and then allowing the slide to cool to room temperature. At the physical interface between crystalline phytosterol particles that had melted, and the surrounding glycerine, the crystalline material was replaced by multiple layers of densely packed spherical phytosterol microparticles having a diameter of about 1 to 2 microns. Some of this microparticle material detached and became free-floating in the glycerine liquid, while the bulk of the microspherule material remained bound to the bulk solid. Following cooling, the sample was examined by polarized light microscopy. In a test tube, the microparticles could be released and dispersed into water using a vortex mixer. When viewed in polarized light, most of the interior portions of the solidified material consisted of radially "checkered" dark and light segmented circles of differing diameters; each segment appearing to have a striated and pleated surface. Upon rotation in the polarized light, both the microparticles and the pleated, radially symmetric segments alternated between appearing bright and dark. It was concluded that the glycerine-complexed phytosterols contained liquid crystalline structure.

Example 2

Glycerine-Phytosterol Stoichiometry in Binary Compositions

An experiment was conducted to determine the "saturation uptake" level during the chemical interaction between phytosterols and glycerine, The saturation uptake level can be either an adsorption phenomenon or a solubility phenomenon. First, the saturation level of glycerine uptake into non-esterified phytosterols was determined. Mixed phytosterols that had been purified from soybean oil, and containing principally beta-sitosterol, campesterol and stigmasterol (Coro-Wise® FG-50), were heated, melted at a temperature of approximately 140-150° C. and cooled to room temperature. Increasing levels of glycerine (approximately 5, 10, 20 and 25 parts by weight) could be adsorbed or dissolved in 100 parts by weight of heated and melted free phytosterols. The evidence for adsorption (or solubility) was that a single melted phase of liquid was visible in heated glass test tubes containing these mixtures, whereas when larger amounts of glycerine were added, the glycerine formed a separate clear phase beneath the melted phytosterols. Upon cooling and solidification of the phytosterol samples containing between approximately 5 and 25 parts by weight of glycerine, the resulting solids were dry to the touch with no apparent free glycerine liquid. When 30, 40 or 50 parts by weight of glycerine were similarly dispersed and mixed with 100 parts by weight of the same heat-melted phytosterols, free glycerine liquid was evident as a separate phase beneath the molten phytosterols in the heated test tubes, and the amount of free glycerine increased as the weight fraction of glycerine was increased. Upon cooling of these samples, the uncomplexed glycerine was evident as an oily residue on the surface of the solids. Therefore, it was estimated that the saturation level for glycerine adsorbed or dissolved in soybean-derived free phytosterols (forming a liquid-solid solution) is between 20 and 30 parts by weight glycerine per 100 parts non-esterified phytosterols.

Example 3

Crystalline Versus Amorphous Phytosterol Morphologies

The chemical interaction between phytosterols and glycerine was investigated using phase contrast and polarized light microscopy to distinguish crystalline from non-crystalline materials. Non-crystalline or "mesophase" materials are intermediate between crystalline and non-crystalline phases. Samples of the above-described melted and cooled mixtures of glycerine (between 10 and 50 parts by weight) were combined with 100 parts phytosterols and were spread out on microscope slides to produce thin coatings for microscopic examination. The first two samples, containing 10 and 20 parts by weight glycerine, appeared entirely crystalline (i.e., they contained optically refracting, sharp edged plate-like crystals). However, the remaining samples containing 30, 40 and 50 parts by weight glycerine per 100 parts free phytosterols were unexpectedly converted to a material having a plastic consistency and an amorphous (non-crystalline) oily appearance upon microscopic examination. However, with transmitted polarized light examination, the amorphous-appearing material (both discrete microspheres and continuous regions) changed in appearance upon rotation of the sample on the microscope stage, with different portions of the sample appearing alternately bright and dark. This behavior is diagnostic for liquid crystalline material that, when fluid, still retains alignment of molecules in local regions.

It was found that 30 parts, but not 15 parts, by weight of glycerine converted 100 parts by weight of free phytosterols from a crystalline state to the amorphous, liquid crystalline state. In further experiments it was determined that 25-30 parts by weight of glycerine also could be combined into heat-melted phytosterols, whereas 40-50 parts of glycerine clearly exceeded the solubility limit.

Example 4

Formation of Phytosterol-Glycerine-Monoglyceride Complexes

A combination of 0.5 parts by weight of food grade glycerine, 1.0 part by weight of vegetable oil-derived phytosterols (Cargill (Minneapolis, Minn.) FG-50 free phytosterols containing at least 90% by weight phytosterols), and 1.0 part by weight of the monoglyceride emulsifier Myvatex 8-60 (Kerry Food Ingredients, Inc., Beloit, Wis., containing approximately 90% monoglycerides and 6% sodium stearate as a processing aid) was heated to approximately 100° C. (its melting point is 80-90° C., considerably less than that of the phytosterol alone ($\geqq$130° C.) and melted together to form a homogeneous liquid mixture. The melt was then allowed to cool to room temperature.

A similar experiment was carried out using a 1:1:1 (w/w) melt-blend of propylene glycol-phytosterol-Myvatex 8-60 (remelting temperature of 85-87° C.). Doubling the amount of propylene glycol (2:1:1) only slightly decreased the remelting temperature (83-85° C.) while making the cooled, solidified amorphous blend softer and somewhat easier to manipulate.

Example 5

Dispersal of Phytosterol-Glycerine-Monoglyceride Compexes in Beverages and Foods PGM complexes were made according to the method described in Example 4. The complexes were dispersed by blending directly in non-fat cow's milk and in regular soy milk. Low to moderate shear force and/or agitation was applied using a Waring blender set at low to medium speed. By visual monitoring, dispersal of the PGM complexes was seen to occur rapidly and completely after mixing into either cold or hot cow's milk or soymilk as described above. The resulting suspensions and emulsions were stable over a period of at least one week when stored under conventional refrigeration at 4° C.

PGM complexes also were prepared using Myverol 18-04 (Kerry Food Ingredients, Inc.) as the emulsifier. Myverol 18-04 also contains glyceryl monostearate and monopalmitate, but without the 6% sodium stearate processing agent found in Myvatex 8-60. The phytosterol complexes prepared with Myverol 18-04 were more difficult to disperse using either vortex agitation or high shear Waring blending when compared to the complexes prepared with Myvatex 8-60. Thus, PGM complexes containing a final level of approximately 2% sodium stearate were more easily and effectively dispersed than similar PGM complexes without sodium stearate.

Example 6

Formation of Phytosterol-Monoglyceride Complexes

For comparison with the PGM complex, glycerine-free mixtures of 1:1 (w/w) monoglyceride (Myvatex 8-60) and phytosterols were produced. The monoglyceride and phytosterols were melted, cooled, and co-crystallized to form "PM" complexes. While the PM complex, like the PG complex, is water-dispersible, it disperses as generally crystalline particles that are much larger, i.e., 20-100 microns in diameter, and therefore less useful in food and beverage formulations than the PGM microparticles. Such larger particles are expected to limit the ability of the phytosterol constituent to commingle with cholesterol at the molecular level in the digestive system, thereby reducing the efficacy of phytosterol-promoted fecal elimination of cholesterol.

Example 7

Glycerine-Monoglyceride Stoichiometry in Ternary Compositions

Phytosterol-glycerine-monoglyceride ternary complexes were made as described in Example 4. However the ratio of glycerine to monoglyceride was varied according to the table below.

| Composition | Phytosterols (weight) | Myvatex 8-60 (weight) | Glycerine (weight) | % Phytosterols (wt/wt % of total) |
|---|---|---|---|---|
| A | 1.00 | 1.00 | 0.70 | 37 |
| B | 1.00 | 0.75 | 0.58 | 43 |
| C | 1.00 | 0.50 | 0.45 | 51 |

Each of the compositions A-C formed microparticles having liquid crystalline structure and good to excellent dispersibility in water. Because composition C contains the highest proportion of phytosterols, it may be particularly useful in volume-limited applications such as dietary supplement gelatin capsules that are typically limited to an approximate 1.0 g capacity in which approximately 0.5 g would be phytosterols.

Each of the foregoing patents, patent applications and references is hereby incorporated by reference.

What is claimed is:

1. An edible composition comprising:
   (i) a non-esterified hydrophobic phytosterol, phytostanol, or a combination thereof (collectively "P"); and
   (ii) glycerine ("G");
wherein P and G are commingled to form, at least in part, a PG molecular complex; and wherein the weight ratio of G:P in the composition is at least 0.05:1; wherein said edible composition is a food, beverage, nutritional supplement, or dietary supplement.

2. The composition of claim 1, wherein P is selected from the group consisting of beta-sitosterol, beta-sitostanol, campesterol, campestanol, stigmasterol, stigmastanol, brassicasterol, brassicastanol, clionasterol and clionastanol, and combinations thereof.

3. The composition of claim 1, wherein P is hydrated, hemi-hydrated, dehydrated or a combination thereof.

4. The composition of claim 1, wherein the molar ratio of G:P is about 1:1 or greater.

5. The composition of claim 1, wherein the comingled P and G are in the form of microparticles having a diameter of about 2 microns or less.

6. The composition of claim 5, wherein said microparticles remain stably dispersed when suspended in an aqueous medium.

7. The composition of claim 1, wherein at least a portion of said PG molecular complex is present in a liquid crystalline form.

8. The composition of claim 1, further comprising a dispersing agent ("M"), wherein the weight ratio of M:P is from about 0.1:1 to about 2:1.

9. The composition of claim 8, wherein the weight ratio of M:P is from about 0.3:1 to about 1:1.

10. The composition of claim 8, wherein M is a monoglyceride, a diglyceride, a lecithin, an ionic surfactant, or a combination thereof.

11. The composition of claim 10, wherein M comprises a monoglyceride selected from the group consisting of glyceryl monostearate, glyceryl monopalmitate, and combinations thereof.

12. The composition of claim 10, wherein M comprises an ionic surfactant present in a concentration from about 1% to about 10% by weight based on the total amount of M.

13. The composition of claim 10, wherein M is an ionic surfactant which is a salt of a fatty acid, wherein the fatty acid is selected from the group consisting of stearic acid, palmitic acid, myristic acid, lauric acid, capric acid, caprylic acid, oleic acid, and combinations thereof.

14. The composition of claim 13, wherein M comprises a monoglyceride and 5% sodium stearate.

15. The composition of claim 13, wherein M comprises hydrolyzed lecithin and an ionic surfactant.

16. The composition of claim 13, wherein the ionic surfactant is sodium stearate.

17. The composition of claim 10, wherein M comprises a lecithin selected from the group consisting of hydroxylated lecithin and hydrolyzed lecithin.

18. The composition of claim 8 which is suitable for use in a beverage, a food item, a dietary supplement, or a liquid food additive.

19. The composition of claim 18 which is suitable for use in a beverage, wherein the beverage is a nutritional beverage.

20. The composition of claim 19, wherein the beverage is cow's milk, sheep's milk, goat's milk, soymilk, almond milk, or coconut milk.

21. The composition of claim 18 which is suitable for use in a food item, wherein the food item is yogurt, cottage cheese, sour cream, soup, salad dressing, tomato catsup, mustard, barbecue sauce, steak sauce, Worcestershire sauce, cocktail sauce, tartar sauce, pickle relish, tomato-based pasta sauce, pizza sauce, prepared chili, or dessert sauce.

22. A beverage, food item, dietary supplement, or liquid food additive comprising the composition of claim 8.

23. The composition of claim 1, wherein the composition is in the form of paste, granules, or powder.

24. The composition of claim 1, wherein P is a plant or vegetable oil-derived phytosterol or phytostanol, a tall oil-derived phytosterol or phytostanol, or a combination thereof.

25. A method of producing the composition of claim 1, the method comprising the steps of:
   (a) mixing one part by weight of P and at least about 0.05 parts by weight of G, and
   (b) heating the mixture, whereby a PG molecular complex is formed.

26. The method of claim 25, wherein step (a) further comprises mixing with P and G about 0.1 to about 2 parts by weight, based on the weight of P, of a dispersing agent ("M").

27. The method of claim 26, wherein said heating is to about 100° C.

28. The method of claim 26, wherein M is a monoglyceride, a diglyceride, a lecithin, or an ionic surfactant.

29. The method of claim 25 wherein, during the step of heating, water of hydration is removed by evaporation or boiling.

30. The method of claim 25, further comprising the step of:
(c) cooling the mixture after step (b).

31. A composition made by the method of claim 26.

32. A composition made by the method of claim 25.

33. A beverage, food item, dietary supplement, or liquid food additive comprising the composition of claim 1.

34. The composition of claim 1, wherein the comingled P and G are in the form of microparticles having a diameter of less than 5 microns.

35. The composition of claim 1, wherein the comingled P and G are in the form of microparticles having a diameter of about 4 microns or less.

36. An edible composition comprising:
(i) a non-esterified hydrophobic phytosterol, phytostanol, or a combination thereof (collectively "P"); and
(ii) glycerine, propylene glycol, or a combination thereof (collectively "G");

wherein P and G are comingled to form, at least in part, a PG molecular complex; and wherein the weight ratio of G to P in the composition is at least 0.05; wherein said edible composition is a food, beverage, nutritional supplement, or dietary supplement.

37. The composition of claim 36, further comprising a dispersing agent ("M"), wherein the weight ratio of M:P is from about 0.1:1 to about 2:1.

* * * * *